US006764854B2

(12) United States Patent
Konzak et al.

(10) Patent No.: US 6,764,854 B2
(45) Date of Patent: Jul. 20, 2004

(54) METHODS FOR GENERATING DOUBLED HAPLOID PLANTS

(75) Inventors: Calvin F. Konzak, Pullman, WA (US);
Enrique A. Polle, Pullman, WA (US);
Weiguo Liu, Pullman, WA (US);
Yuanming Zheng, Pullman, WA (US)

(73) Assignee: Northwest Plant Breeding Company, Pullman, WA (US)

( * ) Notice: Subject to any disclaimer, the term of this patent is extended or adjusted under 35 U.S.C. 154(b) by 208 days.

(21) Appl. No.: 10/042,932

(22) Filed: Jan. 8, 2002

(65) Prior Publication Data

US 2002/0104128 A1 Aug. 1, 2002

Related U.S. Application Data

(63) Continuation of application No. 09/383,588, filed on Aug. 26, 1999.
(60) Provisional application No. 60/099,633, filed on Sep. 9, 1998.

(51) Int. Cl.$^7$ .......................... C12N 15/82; C12N 5/00; C12N 5/02; C12N 15/87; A01N 1/00

(52) U.S. Cl. .................... 435/468; 435/430; 435/430.1; 435/431; 435/421; 435/420; 800/278; 800/299; 800/320.2

(58) Field of Search ................................ 435/468, 430, 435/430.1, 431, 421, 420; 800/278, 299, 3, 260, 271, 268, 275, 320, 320.1

(56) References Cited

U.S. PATENT DOCUMENTS

| 5,049,503 A | | 9/1991 | Swanson et al. | |
|---|---|---|---|---|
| 5,272,072 A | * | 12/1993 | Kaneko et al. | .......... 435/172.3 |
| 5,322,789 A | * | 6/1994 | Genovesi et al. | ........ 435/240.5 |
| 5,445,961 A | | 8/1995 | Genovesi et al. | |
| 5,900,375 A | | 5/1999 | Simmonds et al. | |

OTHER PUBLICATIONS

Kasha et al, "Haploids in Cereal Improvement: Anther and Microscope Culture", Gene Manipulation in Plant Improvement II, Plenum Press, pp. 213–230.*
Kohler and Wenzel, J. Plant Physiol., vol. 121. pp 181–191.*
Armstrong, T.A., S.G. Metz and P.N. Mascia, "Two Regeneration Systems for the Production of Haploid Plants from Wheat Anther Culture," *Plant Science*, vol. 51, pp. 231–237 (1987).
Ball, Shane T., HuaPing Zhou and Calvin F. Konzak, "Influence of 2,4–D, IAA, and duration of callus induction in anther cultures of spring wheat," *Plant Science*, vol. 90, pp. 195–200 (1993).
Ball, S.T., H. Zhou, and C.F.Konzak, "Sucrose Concentration and Its Relationship to Anther Culture in Wheat," *Crop Science*, vol. 32, pp. 149–154 (1992).

Bennett, Michael D., and W. Glyn Hughes, "Additional Mitosis in Wheat Pollen induced by Ethrel," *Nature*, vol. 240, pp. 566–568 (Dec. 1972).
Bin, Huang, "Ultrastructural Aspects of Pollen Embryogenesis in Hordeum, Triticum and Paeonia," in Hu, H. and H.Y. Yang (Eds.), *Haploids of Higher Plants in Vitro,*, China Academic Publishers, Beijing (1986) pp. 91–117.
Chih–ching, Chu, "The N$_6$ Medium and its Applications to Anther Culture of Cereal Crops," *In Proceedings of Symposium on Plant Tissue Culture*, Sci. Press, Peking, China, pp. 43–50 (1978).
Chu, C.C. and R.D. Hill, "An improved anther culture method for obtaining higher frequency of pollen embyroids in *Triticum aestivum* L.," *Plant Science*, vol. 55, pp. 175–181 (1988).
Chu, C.C., R.D. Hill and A.L. Brule–Babel, "High Frequency of Pollen Embryoid Formation and Plant Regeneration In *Triticum aestivum* L. on Monosaccharide Containing Media," *Plant Science*, vol. 66, pp. 255–262 (1990).
Dale, Philip J., "Pollen Dimorphism and Anther Culture in Barley," *Planta*, vol. 127, pp. 213–220 (1975).
Darvey, N.L., "Doubled haploid technology: An interactive model for germplasm enhancement," *Proceedings of the 9th International Wheat Genetics Symposium, Keynote Addresses and Oral Presentations*, vol. 1, Sect. 5—Transgenics (Aug. 2–7, 1998).

(List continued on next page.)

*Primary Examiner*—Anne Marie Grunberg
(74) *Attorney, Agent, or Firm*—Christensen O'Connor Johnson Kindness PLLC

(57) ABSTRACT

The present invention provides methods for generating doubled haploid and/or haploid plants from microspores. In a presently preferred embodiment of the methods of the present invention, plant material is selected that bears reproductive organs containing microspores at a developmental stage that is amenable to androgenic induction. The microspores are treated by contacting the selected plant material with water and subjecting the selected plant material to temperature stress, and optionally to nutrient stress. Preferably the selected plant material is contacted with an effective amount of a sporophytic development inducer and an effective amount of an auxin and/or a cell spindle inhibiting agent. Optionally, the selected plant material is contacted with an effective amount of a cytokinin and/or an effective amount of a gibberellin. The treated microspores are isolated, preferably by density centrifugation utilizing a solution of 0.3 M mannitol layered over a higher density solution of a sugar, preferably maltose. The isolated, treated microspores are then cultured in a liquid nutrient suspension medium supplemented with at least one plant ovary or with an aliquot of plant ovary conditioned medium, until the microspores develop into embryoids. The embryoids are transferred to a regeneration medium and incubated therein until the embryoids develop into plants. The resulting plants may be haploid or doubled haploid and may also be genetically transformed.

35 Claims, No Drawings

OTHER PUBLICATIONS

De Buyser, J., P. Touraine, A. Ambroise and E. Picard, "Induction of androgenetic embryos and chlorophyllian plants of *Triticum aestivum* from isolated microsphere culture," *Proceedings of the 9th International Wheat Genetics Symposium, Poster Presentations*, vol. 3, Sect. 5—Transgenics (Aug. 2–7, 1998).

Devaux, P., "Comparison of Anther Culture and the *Hordeum bulbosum* Method for the Production of Doubled Haploids in Winter Barley," *Plant Breeding*, vol. 100, pp. 181–187 (1988).

Falconer, Marcia M., and R.W. Seagull, "Amiprophos-methyl (APM): A Rapid, Reversible, Anti–microtubule Agent for Plant Cell Cultures," *Protoplasma*, vol. 136, pp. 118–124 (1987).

Gustafson, Vicki D., P. Stephen Baenziger, Martha S. Wright, Walter W. Stroup and Yang Yen, "Isolated wheat microspore culture," *Plant Cell, Tissue and Organ Culture*, vol. 42, pp. 207–213 (1995).

Heberle–Bors, Erwin, "In vitro pollen embryogenesis in *Nicotiana tabacum* L. and its relation to pollen sterility, sex balance, and floral induction of the pollen donor plants," *Planta*, vol. 156, pp. 396–401 (1982).

Heberle–Bors, Erwin, "Induction of embryogenic pollen grains in situ and subsequent in vitro pollen embryogenesis in *Nicotiana tabacum* by treatments of the pollen donor plants with feminizing agents," *Physiol. Plant.*, vol. 59, pp. 67–72 (1983).

Heberle–Bors, Erwin, "On the time of embryogenic pollen grain induction during sexual development of *Nicotiana tabacum* L. plants," *Planta*, vol. 156, pp. 402–406 (1982).

Heberle–Bors, E., "In vitro haploid formation from pollen: a critical review," *Theoretical and Applied Genetics*, vol. 71, pp. 361–374 (1985).

Henry, Y., and J. de Buyser, Effect of the 1B/1R translocation on anther culture ability in wheat (*Triticum aestivum* L.), *Plant Cell Reports*, vol. 4, pp. 307–310 (1985).

http:tdg.uofuelph.ca/CRSC/cereals/culture.htm, "Development of a Functional Microspore Culture System for Barley (*Hordeum vulgare* L.) Cultivars," available at least as early as 1997.

Hu, T.C., A. Ziauddin, E. Simion, and K.J. Kasha, "Isolated Microspore Culture of Wheat (*Triticum aestivum* L.) in a Defined Media," *In Vitro Cell. Dev. Biol.*, vol. 31, pp. 79–83 (Apr. 1995).

Hu, T., and K.J. Kasha, "Improvement of isolated microspore vulture of wheat (*Triticum aestivum* L.) through ovary co–culture," *Plant Cell Reports*, vol. 16, pp. 520–525 (1997).

Jähne, Alwine, and Horst Lörz, "Cereal microspore culture," *Plant Science*, vol. 109, pp. 1–12 (1995).

Junwen, Ouyang, "Induction of Pollen Plants in *Triticum aestivum*," in Hu, H. and H.Y. Yang (Eds.) *Haploids of Higher Plants in Vitro*, , China Academic Publishers, Beijing (1986) pp. 26–41.

Kasha, K.J., T.C. Hu, E. Simion and R. Oro, "Cytological development of wheat microspores in culture," *Proceedings of the 9th International Wheat Genetics Symposium, Keynote Addresses and Oral Presentations*, vol. 1, Sect. 5—Transgenics (Aug. 2–7 1998).

Kasha, K.J., A. Ziauddin and U.–H. Cho, "Haploids in Cereal Improvement: Anther and Microspore Culture," *Gene Manipulation in Plant Improvement II*, Crop Science Dept., Univ. of Guelph. Ontario, Canada, pp. 213–230 (1990).

Köhler, F., and G. Wenzel, "Regeneration of Isolated Barley Microspores in Conditioned Media and Trials to Characterize the Responsible Factor," *J. Plant Physiol.*, vol. 121, pp. 181–191 (1985).

Kyo, M., and H. Harada, "Control of the developmental pathway of tobacco pollen in vitro," *Planta*, vol. 168, pp. 427–432 (1987).

Mejza, Stephen J., Vincent Morgant, Denise E. DiBona, and James R. Wong, "Plant regeneration from isolated microspores of *Triticum aestivum*," *Plant Cell Reports*, vol. 12, pp. 149–153 (1993).

Morejohn, L.C., T.E. Bureau, J. Mole–Bajer, A.S. Bajer and D.E. Fosket, "Oryzalin, a dinitroaniline herbicide, binds to plant tubulin and inhibits microtubule polymerizatin in vitro," *Planta*, vol. 172, pp. 252–264 (1987).

Picard, E., C. Hours, S. Grégoire, T.H. Phan and J.P. Meunier, "Significant improvement of androgenetic haploid and doubled haploid induction from wheat plants treated with a chemical hybridization agent," *Theoretical and Applied Genetics*, vol. 74, pp. 289–297 (1987).

Puolimatka, Matti, Sisko Laine and Janos Pauk, "Effect of ovary co–cultivation and culture medium on embryogenesis of directly isolated microspores of wheat," *Cereal Research Communications*, vol. 24:No. 4, pp. 393–400 (1996).

Reynolds, Thomas L., and Rebecca L. Crawford, Changes in abundance of an abscisic acid–responsive, early cysteine–labeled metallothionein transcript during pollen embryogenesis in bread wheat (*Triticum aestivum*,), *Plant Molecular Biology*, vol. 32, pp. 823–829 (1996).

Touraev, Alisher, Andi Ilham, Oscar Vicente, and Erwin Heberle–Bors, "Stress–induced microspore embryogenesis in tobacco: an optimized system for molecular studies," *Plant Cell Reports*, vol. 15, pp. 561–565 (1996).

Touraev, A., A. Indrianto , I. Wratschko, O. Vicente, E. Heberle–Bors, "Efficient microspore embryogenesis in wheat (*Triticum aestivum*L.) induced by starvation at high temperature," *Sex Plant Reprod.*, vol. 9, pp. 209–215 (1996).

Tuvesson, Inger Kirstine Due, and Rebecka Charlotte Viktoria Öhlund, "Plant regeneration through culture of isolated microspores of *Triticum aestivum* L.," *Plant Cell, Tissue and Organ Culture*, vol. 34, pp. 163–167 (1993).

Vaughn K.C. and L.P. Lehnen, Jr. "Mitotic Disrupter Herbicides," *Weed Science,* 39:450–457, 1991.

Xie, Jiahua, Mingwei Gao, Qihua Cai, Xiongying Cheng, Yuwei Shen and Zhuqing Liang, Improved isolated microspore culture efficiency in medium with maltose and optimized growth regulator combination in japonica rice (*Oryza sativa*), *Plant Cell, Tissue and Organ Culture*, vol. 42, pp. 245–250 (1995).

Zheng, Y. "The effect of 2,4–D in Pre–culture Media Before the Isolation of Microspores for In–Vitro Culture," Chapter 4 of Ph.D. Thesis, Washington State University (1994).

Zhou, Huaping, and C.F. Konzak, "Improvement of Anther Culture Methods for Haploid Production in Wheat," *Crop Sci.*, vol. 29, pp. 817–821 (1989).

Zhou, Huaping, and Calvin F. Konzak, "Genetic control of green plant regeneration from anther culture of wheat," *Genome*, vol. 35, pp. 957–961 (Dec. 1992).

Zhou, H., Y. Zheng and C.F. Konzak, "Osmotic potential of media affecting green plant percentage in wheat anther culture," *Plant Cell Reports*, vol. 10, pp. 63–66 (1991).

* cited by examiner

METHODS FOR GENERATING DOUBLED HAPLOID PLANTS

CROSS-REFERENCES TO RELATED APPLICATIONS

The present application is a continuation of U.S. patent application Ser. No. 09/383,588, filed on Aug. 26, 1999, which claims benefit of priority from U.S. Provisional Patent Application No. 60/099,633, filed on Sep. 9, 1998.

STATEMENT REGARDING FEDERALLY SPONSORED RESEARCH OR DEVELOPMENT

This invention was made with government support under grant USDA-SBIR 97-03374, awarded by the United States Department of Agriculture. The government has certain rights in the invention.

RELATED APPLICATIONS

This application claims benefit of priority from U.S. provisional patent application serial No. 60/099,633, filed on Sep. 9, 1998. invention was funded in part by grant USDA-SBIR 97-03374 from the United States Department of Agriculture. The goverment has certain rights in this invention.

FIELD OF THE INVENTION

This invention relates to methods for generating doubled haploid plants from microspores, and to doubled haploid plants produced by the methods disclosed herein.

BACKGROUND OF THE INVENTION

Although plant breeding programs worldwide have made considerable progress developing new cultivars with improved disease resistances, yields and other, useful traits, breeding as a whole relies on screening numerous plants to identify novel, desirable characteristics. Very large numbers of progeny from crosses often must be grown and evaluated over several years in order to select one or a few plants with a desired combination of traits.

In a typical plant breeding experiment, two parent plants are crossed and the resulting progeny (the F1 generation) are screened and a plant (termed the F1 plant) identified that possesses a desirable combination of phenotypic traits. The F1 plant is then self-fertilized to yield a population of progeny plants (termed F2 plants) that must be individually analyzed to determine which F2 plants possess the desired combination of phenotypic traits originally introduced in the F1 plant. If, as is often the case, the desired phenotypic traits derive from the combined effect of several genes, then the number of F2 progeny plants that must be screened depends on the number of genetic differences between the parents of the F1 plant. Thus, the greater the number of genetically-controlled differences between parents of the F1 plant, the larger the number of F2 progeny that must be grown and evaluated, and the lower the probability of obtaining progeny with all the desired traits.

For example, if the two parents of the F1 plant differ by 25 gene alleles (not an unusually great number in breeding), more land than exists on the earth would be needed to grow all possible genotype combinations which can occur in the F2 generation derived from the self-fertilized F1 plant (Konzak, C. F. et al. In: Elliott, L. (ed.) *STEEP—Conservation Concepts and Accomplishment*, pp. 247–273, 1987.). Further, once an F2 plant has been identified that exhibits the same, desirable, phenotypic trait(s) as the cross parents, the process of self-fertilization and analysis of the resulting progeny must be repeated several times until a homozygous population of plants is obtained which breed true for the desired phenotypic character, i.e., all progeny derived from the true-breeding population exhibit the desired, phenotypic trait (though the progeny may not be true-breeding for unselected traits).

One possible solution to the problem of screening large numbers of progeny is to produce them from the gametic cells as haploid plants, the chromosomes of which can be doubled using colchicine or other means to achieve instantly homozygous, doubled-haploid plants. In particular, doubled haploids can be produced from the microspores which normally give rise to pollen grains.

The life cycle of flowering plants exhibits an alteration of generations between a sporophytic (diploid) phase and a gametophytic (haploid) phase. Meiosis produces the first cells of the haploid generation which are either microspores (male) or megaspores (female). Microspores divide and develop within anthers to become mature male gametophytes (pollen). In normal development, microspores are genetically programmed for terminal differentiation to form mature pollen through two cell divisions. However, under certain conditions, microspores can be induced to initiate sporophytic development which leads to the formation of haploid or doubled haploid "embryoids". These embryoids can give rise to mature plants, that are either haploids or doubled haploids, through subsequent sporophytic development. The process by which plants are produced from microspores is termed pollen-embryogenesis or androgenesis, i.e., from the male gametophyte. Androgenesis is of significant interest for developmental genetic research as well as plant breeding and biotechnology, since it is a means to produce genetically true-breeding, doubled haploid plants.

As shown in Table 1, by producing doubled-haploid (also termed polyhaploid) progeny, the number of possible gene combinations for any number of inherited traits is more manageable.

TABLE 1

Minimum size of F2 population needed to obtain all possible gene combinations with various numbers of independently assorting gene pairs

| | Minimum Population Number Required | |
|---|---|---|
| Number of Independently Assorting Gene Pairs | Conventional Breeding System | Doubled haploid System |
| 1 | 4 | 2 |
| 2 | 16 | 4 |
| 3 | 64 | 8 |
| 4 | 256 | 16 |
| 5 | 1024 | 32 |
| 10 | 1,048,576 | 1024 |
| 20 | 1,099,511,627,776 | 1,048,576 |

Thus, marked improvements in the economics of breeding can be achieved via doubled haploid production, since selection and other procedural efficiencies can be markedly improved by using true-breeding (homozygous) progenies. With doubled haploid production systems, homozygosity is achieved in one generation. Thus, the breeder can eliminate the numerous cycles of inbreeding necessary by conventional methods to achieve practical levels of homozygosity. Indeed, true homozygosity for all traits is not even achievable by conventional breeding methods. Consequently, an efficient doubled haploid technology would enable breeders to reduce the time and the cost of cultivar development relative to conventional breeding practices.

Thus, there is a need for a method of efficiently producing doubled haploid plants that is applicable to a wide variety of plant species.

SUMMARY OF THE INVENTION

In accordance with the foregoing, in one aspect the present invention provides methods of generating doubled haploid and/or haploid plants from microspores.

The methods of the present invention for producing plants from microspores include the steps of: selecting plant material including microspores at a developmental stage amenable to androgenic induction; subjecting the microspores to temperature stress to obtain stressed microspores; contacting the microspores with an amount of a sporophytic development inducer effective to induce sporophytic development and chromosome doubling, the contacting step occurring before, during, after, or overlapping with any portion of the temperature stress step; isolating the stressed microspores; and coculturing the isolated microspores with either ovary-conditioned medium or at least one live plant ovary. Preferably, microspores are subjected to nutrient stress at the same time that they are subjected to temperature stress. Preferably, microspores are contacted with an amount of an auxin and/or a cell spindle inhibiting agent before, during, after, or overlapping with any portion of the temperature stress step.

In the practice of the methods of the present invention, plant material is selected that bears reproductive organs containing microspores at a developmental stage that is amenable to androgenic induction. Preferably the selected plant material is tillers or branches bearing spikes or flowers that contain microspores in the mid uninucleate to early binucleate stages of development. The microspores are treated by contacting the selected plant material with an aqueous medium, such as water, and subjecting the selected plant material to temperature stress, and optionally to nutrient stress. Temperature stress is effected by incubating the selected plant material, in contact with aqueous medium, at a preferred temperature of from about 4° C. to about 40° C., more preferably from about 28° C. to about 35° C., most preferably at about 33° C., for a period of from about half an hour to about 72 hours. Nutrient stress is effected by utilizing, in the aqueous medium, an amount of at least one nutrient (such as nitrogen, calcium, phosphorus or sulfur) that is less than the amount of that nutrient necessary for the optimal growth and development of the microspores. Preferably nutrient stress is effected by utilizing water as the aqueous medium. Most preferably nutrient stress is effected by utilizing diluted NPB 98 as the aqueous medium, preferably NPB 98 medium diluted with an amount of water sufficient to dilute NPB 98 to less than or equal to 80% of its undiluted concentration. The selected plant material is also contacted with an effective amount of at least one sporophytic development inducer (as further described herein), such as 2-hydroxynicotinic acid (2-HNA), violuric acid, 2-hydroxyproline or ethrel. Preferably the selected plant material is contacted with an effective amount of a sporophytic development inducer and an effective amount of an auxin (preferably 2,4-dichlorophenoxyacetic acid) and/or an effective amount of a cell spindle inhibiting agent (such as pronamide). The presently preferred concentration range for auxin is from about 0.1 mg/l to about 25 mg/l, more preferably from about 0.2 mg/l to about 10.0 mg/l, most preferably from about 0.5 mg/l to about 4.0 mg/l. The presently preferred concentration range for sporophytic development inducer is from about 0.001 mg/l to about 1000 mg/l. The presently most preferred concentration range for sporophytic development inducer is from about 1 mg/l to about 500 mg/l. The presently preferred concentration range for cell spindle inhibiting agent is from about 1.0 $\mu$M to about 200 $\mu$M.

Optionally, the selected plant material is contacted with an effective amount of a cytokinin, preferably kinetin or BAP, and/or an effective amount of a gibberellin. The preferred concentration range for cytokinin is from about 0.1 mg/l to about 10 mg/l, more preferably from about 0.2 mg/l to about 4.0 mg/l, most preferably from about 0.5 mg/l to about 2.0 mg/l. The presently preferred concentration range for gibberellin is from about 0.01 mg/l to about 20 mg/l, most preferably from about 0.2 mg/l to about 4.0 mg/l. The selected plant material is contacted with some or all of the foregoing chemical agents (sporophytic development inducer, cell spindle inhibiting agent, auxin, cytokinin and/or gibberellin) before, during, after, or overlapping with any portion of the temperature stress treatment. The treated microspores are isolated preferably by macerating the selected, treated plant tissue, filtering the macerated plant tissue and subjecting the filtrate to density centrifugation, preferably utilizing a solution of percoll, ficoll or mannitol, most preferably a 0.3 M mannitol solution, layered over a higher density solution of percoll, ficoll, polyethylene glycol or a sugar, preferably maltose, most preferably 0.58 M maltose. The isolated, treated microspores are then cultured in a liquid nutrient suspension medium, such as medium NPB98 or NPB 99, preferably NPB 99, supplemented with either plant ovary conditioned medium or at least one live plant ovary, until the microspores develop into embryoids. Preferably the plant ovaries (including the ovaries used to prepare plant ovary conditioned medium) are obtained from wheat varieties "Chris" or "Pavon 76", but ovaries from a wide range of genotypes, including Igri barley, are effective. The embryoids are transferred to a regeneration medium and incubated therein until the embryoids develop into plants. The resulting plants may be doubled haploids, or they may be haploids which can be converted to doubled haploids by treatment with a chromosome doubling agent such as colchicine. It will be understood, however, that the microspores can be isolated before being contacted with an aqueous medium and being subjected to temperature stress.

The methods of the present invention for producing plants from microspores may optionally include the step of genetically transforming the microspores. Microspores can be genetically transformed at any time during treatment of the microspores in accordance with the methods of the present invention. The presently preferred methods of genetically transforming microspores are biolistic gene transfer utilizing a particle gun or electroporation of plasmolyzed microspores. Thus, in one aspect, the present invention provides genetically transformed plants regenerated from microspores.

In other aspects, the present invention provides methods of initiating microspore embryogenesis including the steps of: selecting plant material including microspores at a developmental stage amenable to androgenic induction; subjecting the microspores to temperature stress to obtain stressed microspores; and contacting the microspores with an amount of a sporophytic development inducer effective to induce sporophytic development and chromosome doubling, the contacting step occurring before, during, after, or overlapping with any portion of the temperature stress step.

Preferably, microspores are subjected to nutrient stress at the same time that they are subjected to temperature stress. Preferably, microspores are contacted with an amount of an auxin and/or a cell spindle inhibiting agent before, during, after, or overlapping with any portion of the temperature stress step.

In the practice of the methods of the present invention for initiating microspore embryogenesis, plant material is selected that bears reproductive organs containing microspores at a developmental stage that is amenable to androgenic induction. Preferably the selected plant material is tillers or branches bearing spikes or flowers that contain microspores in the mid uninucleate to early binucleate stages of development. The microspores are treated by contacting the selected plant material with an aqueous medium, such as water, and subjecting the selected plant material to temperature stress, and optionally to nutrient stress. Temperature stress is effected by incubating the selected plant material, in contact with aqueous medium, at a preferred temperature of from about 4° C. to about 40° C., more preferably from about 28° C. to about 35° C., most preferably at about 33° C., for a period of from about half an hour to about 72 hours. Nutrient stress is effected by utilizing, in the aqueous medium, an amount of at least one nutrient that is less than the amount of that nutrient necessary for the optimal growth and development of the microspores. Preferably nutrient stress is effected by utilizing water as the aqueous medium. Most preferably nutrient stress is effected by utilizing diluted NPB 98 as the aqueous medium, preferably NPB 98 medium diluted with an amount of water sufficient to dilute NPB 98 to less than or equal to 80% of its undiluted concentration. The selected plant material is preferably subjected to nutrient stress for a period of from about half an hour to about ninety six hours, more preferably from about half an hour to about seventy two hours. The selected plant material is also contacted with an effective amount of at least one sporophytic development inducer (as further described herein), such as 2-hydroxynicotinic acid (2-HNA), violuric acid, 2-hydroxyproline or ethrel. Preferably the selected plant material is contacted with an effective amount of a sporophytic development inducer and an effective amount of an auxin (preferably 2,4-dichlorophenoxyacetic acid) and/or an effective amount of a cell spindle inhibiting agent (such as pronamide). The presently preferred concentration range for auxin is from about 0.1 mg/l to about 25 mg/l, more preferably from about 0.2 mg/l to about 10.0 mg/l, most preferably from about 0.5 mg/l to about 4.0 mg/l. The presently preferred concentration range for sporophytic development inducer is from about 0.001 mg/l to about 1000 mg/l. The presently most preferred concentration range for sporophytic development inducer is from about 1 mg/l to about 500 mg/l. The presently preferred concentration range for cell spindle inhibiting agent is from about 1.0 $\mu$M to about 200 $\mu$M.

Optionally, the selected plant material is contacted with an effective amount of a cytokinin, preferably kinetin or BAP, and/or an effective amount of a gibberellin. The preferred concentration range for cytokinin is from about 0.1 mg/l to about 10 mg/l, more preferably from about 0.2 mg/l to about 4.0 mg/l, most preferably from about 0.5 mg/l to about 2.0 mg/l. The presently preferred concentration range for gibberellin is from about 0.01 mg/l to about 20 mg/l, most preferably from about 0.2 mg/l to about 4.0 mg/l. The selected plant material is contacted with some or all of the foregoing chemical agents (sporophytic development inducer, cell spindle inhibiting agent, auxin, cytokinin and/or gibberellin) before, during, after, or overlapping with any portion of the temperature stress treatment. It is understood, however, that the microspores can be isolated before being contacted with an aqueous medium and being subjected to temperature stress.

The methods of the present invention for initiating microspore embryogenesis may optionally include the step of genetically transforming the microspores. Preferably uninucleate microspores are used for genetic transformation. Microspores can be genetically transformed at any time during treatment of the microspores in accordance with the methods of the present invention. The presently preferred methods of genetically transforming microspores are biolistic gene transfer utilizing a particle gun or electroporation of plasmolyzed microspores.

In another aspect of the invention, methods are provided for stimulating susceptible plant microspores to form embryoids. The methods include the step of incubating susceptible microspores with at least one whole plant ovary, or with plant ovary conditioned medium capable of stimulating susceptible plant microspores to form embryoids.

In another aspect of the present invention, doubled haploid and/or haploid plants are provided that are produced according to the methods of the present invention.

DETAILED DESCRIPTION OF THE PREFERRED EMBODIMENT

The term doubled haploid (abbreviated as DH) is used herein to refer to plants produced by doubling the chromosome number of a gamete-derived haploid plant which is produced via male gamete sporophytic divisions. The chromosome doubling (including spontaneous chromosome doubling) can occur at any stage in the process of converting a microspore to a whole plant, or can be induced, for example, by treating haploid plants with colchicine.

The term "microspore" refers herein to the male gametophyte of a plant, including all stages of development from meiosis through formation of the mature pollen grain.

The term "androgenic induction" means induction of androgenesis, i.e., the process by which plants are produced from microspores.

The abbreviation mg/l means milligrams per liter.

The methods of the present invention are applicable to a broad range of plant species, including dicotyledonous plants and monocotyledonous plants. Representative examples of plants which can be treated in accordance with the methods of the present invention include, but are not limited to: wheat, barley, rice, corn, triticale, rye, millet, rice, flax, wheat grasses (for example, *Agropyron, Elytrigia*), pasture grasses, rye, orchard and brome grasses (e.g., *Lolium* spp.), turf grasses (e.g., *Poa pratensis*), alfalfa, clover, soybeans, peanuts, ornamentals including garden and commercial flower and bulb species, fruit trees and nut trees, vegetable species (e.g., cucurbits, onions, tomato, carrot, potato and other solanaceous plants, beans, peas, lentils), Brassica species such as oil seed rape, as well as interspecies hybrids (e.g., triploids, pentaploids, tetraploids, hexaploids, septaploids). The methods of the present invention can be used, for example, to produce inbred lines for use in hybrid seed production, especially to generate vigorous inbred lines from hybrids of crop plants that are susceptible to inbreeding depression. Additionally, the methods of the present invention can be used, for example, to obtain variable progeny from pollen-producing apomictic species, such as blue grasses (Poa spp.) and buffalo grasses (Buchloe spp.).

Preferably, the methods of the present invention utilize wheat spikes as starting material. The methods of the present invention have been successfully applied to spikes from a range of wheat genotypes including, but not limited to: the spring wheats, Calorwa, Chris, Pavon 76, Penawawa, Spillman, Waldron, WED 202-16-2, Wawawai, SWSW96005, and winter wheats Claire, Eltan, Platte, Enola, Soisson, BonPain, Madsen and Svilena. The presently preferred wheat genotypes are Chris, WED 202-16-2 and Pavon 76. Spring wheat cv Pavon 76 is generally considered to be a highly androgenic genotype based upon results from anther culture, although it produces a high proportion of albino plants, and a relatively low frequency of doubled haploid plants. The androgenic microspores of both Chris and WED 202-16-2 produce high numbers of green progeny, many of which are spontaneously DH. The presently most preferred wheat cultivar is Chris. Chris is a public variety and Pavon 76 is available from the USDA Cereals Collection, 1691S 2700W, Aberdeen Id. 83210. WED 202-16-2 is a *T. dicoccoides*/Pavon 76 derivative from the Volcani Institute, Bet Degan, Israel.

The methods of the present invention permit the production of doubled haploid plants from wheat varieties and cultivars that have long been considered recalcitrant or non-responsive to anther or microspore culture. For example, Waldron is a spring wheat considered recalcitrant to established anther culture methods. Nonetheless, Waldron is responsive to the methods of the present invention.

In many cases, wheat cultivars that are recalcitrant to other methods, such as Waldron and WPB926, can be induced to begin sporophytic divisions at a high frequency utilizing the methods of the present invention. Microspore cell divisions of some of the less responsive genotypes are arrested prior to the emergence of a multi-nucleate pro-embryoid from a common microspore cell wall. A solution to this problem provided by the present invention is to treat plant material containing microspores with novel culture media NPB 98 or NPB 99, the compositions of which are set forth in Table 6.

An alternative solution to the problem of arrested microspore cell divisions is to make crosses between the recalcitrant cultivars, such as Waldron or WPB 926, and cultivars that efficiently produce green plants from embryoids, such as Chris and WED 202-16-2. In this approach, the methods of the present invention can be incorporated into a more general plant breeding program in which genotypes that are amenable to culture according to the methods of the present invention are crossed with less amenable genotypes which have other, desirable characteristics. For example, Pavon 76, which produces many embryoids, but relatively few green plants when treated in accordance with the methods of the present invention, can be crossed with WED 202-16-2, Chris, or any other wheat genotype which produces a high frequency of green plants from embryoids when treated in accordance with the methods of the present invention. The resulting doubled haploid progeny can be screened for those genotypes that produce many embryoids and many green plants. Similarly, crossing Chris, Pavon 76 or WED 202-16-2 with a recalcitrant genotype will result in progeny that are amenable to culture according to the methods of the present invention, and which also possess the desirable traits of the recalcitrant parent. The strategy of crossing a genotype that is amenable to the production of green, double haploid plants with a more recalcitrant plant species, having some other desirable trait(s), is generally applicable to any plant species.

The recalcitrant genotypes especially respond to culture in NPB 98 or NPB 99 that is conditioned by the prior growth of plant ovaries at a density of 3 to 4 ovaries per milliliter of medium for 7 to 14 days prior to use in microspore culture. Media so conditioned have been shown to accelerate cell divisions and embryogenic development of cultured micrspores. Typically, mature embryoids can be obtained one week earlier than in cultures that utilize whole ovaries instead of ovary-conditioned medium.

Wheat plants that are used to provide the microspore starting material (referred to as donor plants) in the practice of the presently preferred embodiment of the present invention may be cultivated in the field, but preferably are cultivated in an artificial, relatively sterile environment, such as a greenhouse. Field-grown wheat plants are often heavily infested with microorganisms that contaminate all stages of the microspore embryogenic process, unless an effective disinfectant treatment is used. For example, the starting plant material used in the methods of the present invention can be treated with a 20% (v/v) solution of commercial hypochlorite or chlorine bleach. Any standard growth regime that is known to one of ordinary skill in the art for growing wheat, preferably in a greenhouse, can be utilized in the practice of the present invention.

In the presently preferred embodiment of the present invention, fresh wheat tillers are cut below the top two nodes. The use of whole tillers avoids the difficulty and inconvenience associated with isolating anthers prior to treatment. The selected tillers should contain microspores at the appropriate stage of development. In general, developing microspores that have at least completed meiosis are useful in the practice of the present invention. Preferably, microspores enclosed within the anthers in the middle section of a spike should be in the mid uninucleate to early binucleate stages, most preferably in the late uninucleate stage, of development. Morphological features of tillers containing microspores at these stages can easily be established for each plant variety by comparing the morphology of the tiller with the microspore developmental stage as determined by microscopic examination with acetocarmine stain. The stages of microspore development are set forth in Bennett, M. D. et al., *Philosophical Transactions of the Royal Society* (Lond.), B issue, 266:39–81 (1973), which is incorporated herein by reference. The morphology of a wheat tiller is set forth in the following publications, each of which is incorporated herein by reference: Percival, J., *The Wheat Plant, A Monograph*, E. P. Dutton & Co., New York (1921); Montana State University Bulletin 4387, and University of Idaho Series 118.

Excised tillers are subjected to stress treatment, such as nutrient and/or temperature stress, treatment with sporophytic development inducers, and optionally to treatment with auxins, cell spindle inhibiting agents, cytokinins and gibberellins as is herein described. In one representative embodiment, leaves are removed from the selected tillers, and the tillers are placed in a flask, preferably an Ehrlenmeyer flask, containing sterile, distilled water. Several tillers may be placed in the same flask. The flask containing the tillers is placed inside a thin plastic bag, which is placed in an incubator at the appropriate temperature for stress treatment. Alternatively, the flask containing tillers can be stored in a refrigerator at 4° C. for up to 1 month before subjecting the tillers to temperature stress treatment. Temperature stress is carried out preferably from between about 4° C. to about 40° C. The optimum period of pretreatment varies with the genotype, but is preferably from between about 0.5 hours and about 72 hours. Also, in general, the higher the temperature used to stress the plant material, the shorter will be the time required to temperature stress the plant material. Alternatively, microwave radiation (having an energy of $10^{-6}$ to $10^{-3}$ eV) can be used to subject the microspores to temperature stress. Nutrient stress is effected by utilizing, in the aqueous medium, an amount of at least one nutrient that is less than the amount of that nutrient necessary for the optimal growth and development of the microspores in the aqueous medium. Preferably nutrient stress is effected by utilizing water as the aqueous medium. Most preferably nutrient stress is effected by utilizing diluted NPB 98 as the aqueous medium, preferably NPB 98 medium diluted with an amount of water sufficient to dilute NPB 98 to less than or equal to 80% of its undiluted concentration. Nutrient stress is one way in which to promote the induction of sporophytic development from microspores and can be used, for example, when dealing with microspores from plant genotypes that are resistant to androgenic induction.

It is important that after stress treatment, the tillers should not be stored in a refrigerator at 4° C. because the microspore viability decreases sharply. After the stress treatment, plant material should be processed as soon as possible. The flask with tillers is removed from the incubator after temperature stress and the spikelets from each spike are excised and the microspores isolated as described more fully herein.

In order to increase the yields of androgenic microspores induced by the stress treatments, the microspores in the tillers are contacted with an effective amount of a sporophytic development inducer. Most preferably, the microspores in the tillers are contacted with an effective amount of a sporophytic development inducer and an effective amount of an auxin and/or a cell spindle inhibiting agent. Optionally the microspores in the tillers are contacted with an effective amount of a cytokinin and/or a gibberellin. The microspores are contacted with the foregoing chemical agents before, during, after, or overlapping with any portion of the temperature stress treatment. Preferably the microspores are contacted with the foregoing chemical agents before the temperature stress treatment.

Sporophytic development inducers useful in the practice of the present invention induce plant microspores to switch from gametophytic development to sporophytic development. By way of non-limiting example, sporophytic development inducers useful in the practice of the present invention may cause the development of inviable pollen grains, multicellular or multinucleate pollen grains, arrest starch formation in developing microspores and cause physical deformation of mature pollen grains that develop from microspores treated with a sporophytic development inducer. Many sporophytic development inducers useful in the practice of the present invention are chemical hybridizing agents. Chemical hybridizing agents (abbreviated as CHAs) are chemicals which when applied to plants cause the plants to produce inviable pollen. Other sporophytic development inducers useful in the present invention include, but are not limited to: amiprophos methyl, 2-aminonicotinic acid; 2-chloronicotinic acid; 6-chloronicotinic acid; 2-hydroxynicotinic acid; 6-hydroxynicotinic acid; 3-hydroxypicolinic acid; Benzotriazole; 2,2'-dipyridil; 2,4-pyridine dicarboxylic acid monohydrate; 2-hydroxypyridine; 2,3-dihydroxypyridine; 2,4-dihydroxypyrimidine-5-carboxylic acid; 2,4-dihydroxypyrimidine-5-carboxylic acid hydrate; dinitroaniline, phosphoric amide, 2-hydroxypirimidine hydrate; 2,4,5-trihydroxypyrimidine; 2,4,6-trichloropyrimidine; 2-hydroxy-4-methyl pyrimidine hydrochloride; 4-hydroxypyrazolo-3,4,d-pyrimidine; quinaldic acid; violuric acid monohydrate; thymine; xanthine; salicylic acid; sodium salicylate; salicyl aldehyde; salicyl hydrazide; 3-chlorosalicylic acid; fusaric acid; picolinic acid; butanediene monoxime; di-2-pyridyl ketone; salicin; 2,2'-dipyridil amine; 2,3,5-triiodobenzoic; 2-hydroxy pyridine-N-oxide; 2-hydroxy-3-nitropyridine; benzotriazole carboxylic acid; salicyl aldoxime; glycine; D L-histidine; penicillamine; 4-chlorosalicylic acid; 6-aminonicotinic acid; 2,3,5,6-tetrachloride 4-pyridine carboxylic acid; alpha benzoin oxime; 2,3-butadiene dioxime; isonicotinic hydrazide; cupferron; ethyl xanthic acid; 3-hydroxy benzyl alcohol; salicyl amide; salicyl anhydride; salicyl hydroxamic acid; methyl picolinic acid; 2-chloro pyridine; 2,6-pyridine carboxylic acid; 2,3-pyridine dicarboxylic acid; 2,5-pyridine dicarboxylic acid; Monsanto pyridones sold under the trade names Fenridazon and Genesis; pichloram; ammonium thiocyanate; amiben; diethyl dithiocarbamate; glyphosate; anthranilic acid; thiourea; 2,4-diclorophenoxyacetic acid; 4-chloro anisole; 2,3-dichloroanisole; 2-(2,4)-dichlorophenoxy propionic acid; 2-(4-chlorophenoxy)-2-methyl propionic acid; 2-(para-chloro phenoxy)isobutyric acid and α,β-dichlorobutyric acid.

The presently preferred sporophytic development inducers are: 2-hydroxynicotinic acid (2-HNA); 2-chloroethylphosphonic acid (having the commercial name of Ethrel) available from Sigma Chemical Co., PO Box 14508, St. Louis, Mo. 63178–9916; violuric acid monohydrate, 2-chloronicotinic acid and 2-hydroxyproline. The presently most preferred sporophytic development inducers are 2-hydroxynicotinic acid (2-HNA) and 2-chloroethylphosphonic acid. In the practice of the invention, a sufficient amount of the sporophytic development inducer is employed to effect a measurable induction of sporophytic development. The presently preferred concentration range of sporophytic development inducer is from about 0.001 mg/l to about 1000 mg/l.

While not wishing to be bound to a particular theory explaining the method of action of the sporophytic development inducers useful in the practice of the present invention, the presently preferred, representative sporophytic development inducers have some metal chelation ability. In particular, the foregoing, representative sporophytic development inducers can chelate Cu, Mg, Fe and Zn ions. Copper is essential to pollen fertility (Scharrer, K., and Schaumlaufel, E., Z. Pflanz. Dung. Bodenk, 89:1–17 (1960); see also, Tomasik, P. and Ratajewicz, Z., In: Newkome, G. R., and Strekowski, L., (eds.) Chapter 3, Pyridine-metal complexes, pp. 186–409 (1986)).

Preferably, the microspores are also contacted with an amount of an auxin effective to maintain callus development. Representative examples of auxins useful in the practice of the present invention include, but are not limited to: 2,4-dichlorophenoxyacetic acid (2,4-D), as well as related auxins (e.g., indoleacetic acid (IAA), indolebutyric acid (IBA), naphthalene acetic acid (NAA), analogues and/ or salts of 2,4-D). The presently preferred concentration range for auxin is from about 0.1 mg/l to about 25 mg/l, more preferably from about 0.2 mg/l to about 10 mg/l, most preferably from about 0.5 mg/l to about 4.0 mg/l. The microspores are also preferably contacted with an amount of a cell spindle inhibiting agent effective to double the chromosome number in a measurable number of microspores. Cell spindle inhibiting agents (tubulin inhibitors) are auxinlike herbicides of which the presently most preferred is Pronamide (3,5-Dichloro [N-1,1-Dimethyl-2-propynil] benzamide) sold by Chem Service Inc., PO Box 599, West Chester Pa. 19381-0599. The presently preferred concentration range for cell spindle inhibiting agents is from about 1.0 $\mu$M to about 200 $\mu$M.

Optionally microspores treated in accordance with the present invention can be contacted with an amount of a cytokinin effective to improve callus quality, in particular to enhance the ability of callus tissue to grow and to increase the size to which callus tissue develops. Representative examples of cytokinins useful in the practice of the present invention include, but are not limited to: kinetin, benzaminopurine (BAP) and zeatin. Kinetin is the presently preferred cytokinin. Additionally, water in which peeled *Solanum tuberosum* potatoes have been boiled contains significant amounts of cytokinin(s) which can be utilized in the practice of the present invention. The presently preferred concentration range for kinetin, zeatin and BAP is from about 0.1 mg/l to about 10 mg/l, more preferably from about 0.2 mg/l to about 4.0 mg/l, most preferably from about 0.5 mg/l to about 2.0 mg/l.

In yet another embodiment of the present invention, the microspores can be contacted with an amount of a gibberellin effective to enhance cell expansion. The presently preferred concentration range for gibberellin is from about 0.01 mg/l to about 20 mg/l, more preferably from about 0.2 mg/l to about 4.0 mg/l.

The sporophytic development inducer and auxin interact with the aforedescribed temperature and/or nutrient stress treatments to enhance the induction of androgenic microspores. In addition, the sporophytic development inducer and auxin treatments contribute to the completion of androgenesis leading to the eventual formation of mature embryoids which, upon transfer to semi-solid medium, regenerate into green or doubled haploid plants. Obtaining enlarged microspores with a fibrillar cytoplasmic structure is a pre-requisite for embryogenesis, but only those that proceed to proembryoids will eventually develop into mature embryoids, which are then able to regenerate to produce plants. Further, it will be understood that the sporophytic development inducers, auxins, cytokinins, gibberellins and temperature and nutrient stresses described herein act synergistically to produce embryoids from microspores.

An alternative to the use of whole tillers (when wheat is being treated in accordance with the methods of the present invention) is to apply a sporophytic development inducer, and preferably at least one auxin and/or cell spindle inhibiting agent, and optionally a cytokinin and/or a gibberellin, to at least one flag leaf of a spike. The flag leaf painting technique is especially suited for applications to tillers with young spikes bearing developing microspores nearer the stage of meiosis. In the presently preferred flag-leaf painting method, a solution containing a sporophytic development inducer, and preferably at least one auxin and/or cell spindle inhibiting agent, and optionally a cytokinin and/or a gibberellin, is applied to the flag leaf of the spikes, using photographic tongs with a piece of synthetic sponge attached to each fork. The sponge pieces are dipped in the solution containing a sporophytic development inducer, and preferably an auxin and/or cell spindle inhibiting agent, and optionally a cytokinin and/or a gibberellin. For treatment, the tongs are placed such that the flag leaf is between, and in contact with, the two sponge pieces, allowing both sides of the flag leaf to be treated. The leaf is held at its tip by a finger, and is treated twice, once on the down stroke, and once lightly on the up stroke to remove excess chemical solution. The treated tillers are left on the plants until the microspores are judged to be near the late uninucleate stage of development. Then the tillers are removed, and placed in sterile distilled water, and subjected to the aforedescribed temperature and, optionally, nutrient stress treatments. The presently preferred working concentration ranges for the solution(s) of auxin, cell spindle inhibiting agent, sporophytic development inducer, cytokinin and gibberellin are as set forth above.

Treated tillers are macerated, preferably by blending in a Mini-Waring blender, and the liberated microspores are isolated by density gradient centrifugation, preferably utilizing a density gradient constructed from 0.3 M mannitol over a 0.58 M solution of maltose.

In an alternative embodiment of the present invention, microspores are first isolated, preferably by the foregoing density centrifugation procedure. The isolated microspores are placed in water and are then subjected to temperature and, optionally, nutrient stress, in the presence of a sporophytic development inducer, preferably in the presence of a sporophytic development inducer and an auxin and/or a cell spindle inhibiting agent, and optionally in the presence of a cytokinin and/or a gibberellin. The preferred temperature range and duration of temperature stress treatment, and the preferred concentrations of auxin, sporophytic development inducer, cytokinin and gibberellin, are as set forth above.

The isolated, treated microspores are then cultured in the presence of at least one live plant ovary or in the presence of an aliquot of plant ovary conditioned medium. Presently preferred sources of ovaries are wheat cultivars Pavon 76 and Chris. It has been found that the plant ovaries do not have to be from the same variety (genotype) or species as the plant from which the embryoids are generated. Thus, for example, ovaries from Igri winter barley, or NPB96001 oats, will stimulate the development of wheat embryoids.

Typically 3 to 6 live plant ovaries will be added to a 60 mm diameter Petri dish containing approximately 5 ml of embryoid culture medium. The presently preferred embryoid culture medium is NPB 99, the composition of which is set forth in Example 6 herein. Preferably the embryoid culture medium osmolarity should be around 300 mOsmo.

Alternatively, an aliquot of plant ovary conditioned medium can be used instead of live plant ovaries, as exemplified in Example 7 herein. It is understood that the use of whole, live ovaries together with an aliquot of plant ovary conditioned medium is within the scope of the present invention.

Embryoids develop from treated microspores, in the presence of at least one plant ovary (or in the presence of an aliquot of plant ovary conditioned medium), usually after 3–4 weeks. The developed embryoids are transferred to a regeneration medium, such as media 190-2 and 190-2(*b*) set forth in Example 6, and the remaining, less-developed embryoids are further incubated with fresh ovaries until mature embryoids form. The presently most preferred regeneration medium is 190-2(*b*).

Microspores (preferably uninucleate microspores) treated in accordance with the methods of the present invention can optionally be genetically transformed by any art-recognized means in order to produce plants that express one or more desirable proteins. Examples of techniques for introducing a gene, cDNA, or other nucleic acid molecule into microspores include: transformation by means of *Agrobacterium tumifaciens*; electroporation-facilitated DNA uptake in which an electrical pulse transiently permeabilizes cell membranes, permitting the uptake of a variety of biological molecules, including recombinant DNA, by microspores; microinjection of nucleic acid molecules directly into microspores; treatment of microspores with polyethylene glycol; and bombardment of cells with DNA-laden microprojectiles which are propelled by explosive force or compressed gas to penetrate the microspore and enter the cell nucleus.

An example of a microspore transformation technique that utilizes *Agrobacterium tumifaciens* and is broadly applicable to numerous plant species is disclosed in European Patent Application EP 0 737 748 A1. Isolated microspores are cocultivated with Agrobacterium containing a Ti plasmid including a transgene (within the transfer DNA of the Ti plasmid) that is to be transferred and stably integrated into the microspore genome. Cellulytic enzymes (such as cellulase, hemicellulase and pectinase) are added during the cocultivation step and serve to permeabilize the microspore cell wall. The transfer DNA (T DNA) is transferred from the Agrobacterium cells to the microspores where it is inserted into the microspore genome thereby generating stably genetically transformed microspores. Thereafter, the treated microspores are washed with a mucolytic enzyme (such as lysozyme). Whole plants can then be regenerated from the genetically transformed microspores in accordance with the present invention. Other workers have reported the use of Agrobacterium to successfully transform microspores from Brassica (Pechan P. M., *Plant Cell Rep.* 8:387–390 (1989); Swanson E. B. and Erickson L. R., *Theor. Appl. Genet.* 78:831–835 (1989)).

An example of electroporation-facilitated permeabilization of microspores is reported in Joersbo et al., *Plant Cell, Tissue and Organ Culture* 23:125–129 (1990). Joersbo et al. report the transient electropermeabilization of barley microspores to the dye propidium iodide by delivering rectangular electrical pulses to microspores in a chamber with cylindrical coaxial electrodes at a distance of 1 mm. The electroporation treatment had limited deleterious effect on the microspores which could be cultured to produce green plants. Similarly, Fennell and Hauptmann (*Plant Cell Reports* 11:567–570 (1992)) reported the electroporation-mediated delivery of plasmid DNA into maize microspores, and also reported the polyethylene glycol (PEG)-mediated delivery of plasmid DNA into maize microspores.

A presently preferred method for stably genetically transforming microspores is biolistic transformation whereby microspores are bombarded with DNA-laden microprojectiles which are propelled by explosive force or compressed gas to penetrate the microspore. Yao et al. (*Genome* 40(4) :570–581 (1997)) report the production of transgenic barley plants by direct delivery of plasmid DNA into isolated microspores using high velocity microprojectiles. The plasmid used to transform the microspores contained a bar gene, under the control of a maize ubiquitin promoter, that conferred resistance to the herbicide bialaphos. Thus, genetically transformed microspores or embryoids could be selected based on their resistance to bialaphos present in the culture medium. Similarly, Jahne et al. (*Theor. Appl. Genet.* 89:525–533 (1994)) also report the production of transgenic barley plants by direct delivery of plasmid DNA into isolated microspores using high velocity gold microprojectiles. Again, genetically transformed microspores or microspore-derived calli were selected based on their resistance to bialaphos present in the culture medium. Fukuoka et al. (*Plant Cell Reports* 17:323–328 (1998)) report the production of transgenic rapeseed plants by direct delivery of plasmid DNA into isolated microspores using high velocity microprojectiles. Transformed embryos derived from the microprojectile bombarded microspores were identified by expression of a firefly luciferase gene. Harwood et al. (*Euphytica* 85:113–118 (1995)) disclose the use of the PDS1000 He particle delivery system to genetically transform barley microspores. The gus reporter gene was used to demonstrate both transient and stable transformation events. Additional examples of microspore transformation techniques are set forth in In Vitro Haploid Production in Higher Plants, Chapt. 2, Jain et al. (eds.), Kluwer Academic Publishers (1996). The aforementioned publications disclosing microspore transformation techniques are incorporated herein by reference, and minor variations make these technologies applicable to a broad range of plant species.

In each of the foregoing transformation techniques, DNA from a plasmid is genetically engineered such that it contains not only the gene of interest, but also selectable and screenable marker genes. A selectable marker gene is used to select only those microspores that have integrated copies of the plasmid (the construction is such that the gene of interest and the selectable and screenable genes are transferred as a unit). The screenable gene provides another check for the successful culturing of only those microspores or microspore-derived embryoids carrying the gene(s) of interest. A commonly used selectable marker gene is neomycin phosphotransferase II (NPT II). This gene conveys resistance to kanamycin, a compound that can be added directly to the growth media on which the microspores grow. Plant cells are normally susceptible to kanamycin and, as a result, die. The presence of the NPT II gene overcomes the effects of the kanamycin and each cell with this gene remains viable. As noted above, another selectable marker gene is a gene, such as the bar gene, which confers resistance to a herbicide. A screenable gene commonly used is the $\beta$-glucuronidase gene (GUS). The presence of this gene is characterized using a histochemical reaction in which a sample of putatively transformed cells is treated with a GUS assay solution. After an appropriate incubation, the cells containing the GUS gene turn blue. Preferably, the plasmid will contain both selectable and screenable marker genes.

Plants produced in accordance with the methods of the present invention can be doubled haploids, the chromosome number of which doubled during the androgenesis induction phase of development of whole plants from microspores. Additionally, plants produced in accordance with the methods of the present invention can be haploids, the chromosome number of which can subsequently be doubled by treatment with an agent such as colchicine.

In the experience of the inventors, the methods of the present invention are at least approximately 500-fold more efficient than other methods for producing plants from microspores, efficiency being measured as the percentage of microspores that yield green plants.

The following examples merely illustrate the best mode now contemplated for practicing the invention, but should not be construed to limit the invention.

EXAMPLE 1

Generating Doubled Haploid Wheat Plants from Microspores

Growing Wheat Plants. One to three plants per pot (20 by 25 cm in diameter) are grown in a greenhouse controlled at 29° C.+/–2° C., at a light regime of 17 hours light and 7 hours dark. Fertilizers (N, P, K) are premixed with soil at the time of sowing the seeds. Further application of fertilizer is achieved by daily watering which contains liquid forms of nitrogen (N), phosphorus (P) and potassium (K). In general, any standard conditions for growing wheat in a greenhouse are acceptable provided that quality donor plants can be harvested.

Collecting Tillers. Fresh tillers that contain microspores at an appropriate developmental stage are cut from below two nodes, counted from the top of the tiller, and immediately placed in a clean container with distilled water. All leaves are removed by cutting at their bases. The time between the collection of tillers and their treatment is preferably minimized to reduce the possibility of contamination by microorganisms. Microspores enclosed within the anthers in the middle section of a spike should preferably be in the mid to late uninucleate stage of development. Morphological features of tillers containing microspores at these stages can easily be established for each plant variety via microscopic examination with acetocarmine stain. Fresh tillers so collected are then ready for pretreatment.

Pretreatment of Spikes. After removing the lower nodal section, the collected tillers are placed in an autoclaved sterile flask, containing 50 ml of sterile (autoclaved) distilled water and preferably 0.1% (w/v) 2-HNA and $10^{-6}$ to $10^{-5}$ M 2,4-D. The open end of a plastic bag (thin-walled, grocery store bag) is then wrapped around the neck of the flask and sealed around the neck with masking tape to prevent microbial contamination and excessive loss of water. The flask is then placed in an incubator set at the desired stress temperature, optionally 33° C., but the temperature employed may be higher or lower. The optimum period of pretreatment varies with the genotype, but is preferably from between about 0.5 hours and about 72 hours, depending on the temperature. A presently preferred temperature pretreatment regime is from about 48 hours to about 72 hours at a temperature of about 33° C. The flask containing tillers can also be stored in a refrigerator at 4° C. for up to 1 month before subjecting the microspores to temperature stress treatment. It is important that after the temperature stress treatment, the tillers should not be stored in a refrigerator at 4° C. because the microspore viability goes down sharply.

After the treatment, the embryogenic microspores typically have eight or more small vacuoles immediately enclosed by the cell wall. These vacuoles surround the condensed cytoplasm in the center, forming a fibrillar structure. The embryogenic microspores are usually, but not always, of a larger size (about 50 microns in diameter) than the average non-treated microspores (25–30 microns in diameter).

Microspore Isolation. After the tillers have been pretreated in accordance with the methods set forth herein, they are removed from the treatment flask in a Laminar Flow Hood. All foliage beneath the first tiller node is removed, keeping only the boot containing the spike. Isolated boots are placed on a paper towel and sprayed with 75% ethanol to saturation. The boots are then wrapped in the towel and placed aside in the hood for approximately 45 minutes, or until the ethanol has fully evaporated. Alternatively, isolated boots are disinfected by being immersed in 20% commercial bleach in a cylinder for 20 minutes, followed by rinsing with distilled water two times.

The spikes are aseptically removed from each disinfected boot and each is placed on top of a 125 ml Waring blender cup that has been autoclaved. Awns (if present), and the upper spikelets are removed, using sterile forceps and scissors. Then, florets are cut from their bases and allowed to drop into the open blender-cup. Florets obtained from one to three spikes may be used for each run of the blending process.

Forty ml of a 0.3 M mannitol solution is added to the blender-cup, then a sterilized cap is placed on the blender-cup which is assembled to the blender. The florets are blended for 20 seconds at a low speed (2200 rpm). The blended slurry is poured from the blender-cup into an autoclaved filter (a container with 100 $\mu$m metal mesh at the bottom). The blender-top is rinsed twice with 5 ml of a sterile 0.3 M mannitol solution per rinse, and the mannitol solution is poured into the filter. Residue trapped on top of the filter is discarded, and the filtrate is pipetted into 15 ml sterile centrifuge tubes and centrifuged at 100×g for 3 min.

The supernatant is discarded from the tubes, and the pellets are combined and resuspended in 2 ml of sterile 0.3 M mannitol solution. The resuspended pellets are layered over 5 ml of an autoclaved 0.58 M maltose solution (sterile) and centrifuged at 100×g for 3 minutes. Three ml of the upper band (containing microspores) is collected and resuspended in 10 ml of a sterile 0.3 M mannitol solution in a 15 ml centrifuge tube. The lower band (junk pellet) is resuspended in 12 ml sterile water in a separate 15 ml centrifuge tube.

Both centrifuge tubes are centrifuged at 100×g for 3 min. The supernatant is discarded and the pellet is resuspended in 3 ml filter-sterilized culture medium for upper band microspores, or 3 ml water for lower band junk microspores. The number of microspores in each band is counted with a haemocytometer, and after counting, the lower band junk microspores are discarded. The total of microspores is the sum of the microspores from both the upper band and the lower band. Only the microspores from the upper band are used for culture. The junk (lower band) microspores appear to be those with starch, which were past the stage of development useful in the practice of the present invention. The density-gradient centrifugation serves to separate the androgenic from the non-androgenic microspores, because the androgenic microspores are vacuolate, and are thus less dense, and therefore float above the remaining microspores.

The upper band microspores are resuspended in 10 ml of filter-sterilized culture medium in a 15 ml centrifuge tube and centrifuged at 100×g for 3 min. The supernatant is discarded and the pellet is resuspended in culture medium at a concentration of approximately $1\times10^4$ microspores/ml.

Culture of isolated microspores. Isolated microspores are cultured in liquid NPB 98–1 medium or liquid NPB-99 medium, preferably liquid NPB-99 medium, as a suspension culture. The compositions of NPB 98-1 medium and NPB-99 medium are set forth in Table 6. An aliquot of 2 ml media per 35 mm×10 mm Petri dish, or 5 ml media per 60 mm×15 mm Petri dish, at a density of approximately $1.5\times10^4$ microspores per ml is effective. Immature ovaries are added to the culture at a density of one per ml of medium immediately preceding the incubation. Ovaries are aseptically picked out from fresh and disinfected spikes. Ovaries of all genotypes are effective for the present invention, but the ovaries from varieties Chris or Pavon 76 are preferred for embryogenesis of all wheat varieties tested. The Petri dish is sealed with parafilm and incubated in the dark at 27° C.

Embryogenic microspores begin their first cell division after approximately 12 hr in culture. Multi-cellular proembryoids, still enclosed within the microspore wall or exine, are formed in approximately one week. In approximately one more week, the exine wall ruptures and immature embryoids emerge, which grow into mature embryoids within about 10 to 14 days. Obtaining enlarged microspores with a fibrillar cytoplasmic structure is a pre-requisite for embryogenesis, but only those that proceed to proembryoids will eventually develop into mature embryoids, which are then able to regenerate to produce plants.

When embryoids reach the size of 1 to 2 mm, they are transferred aseptically to solid 190-2 or 190-2(b) medium, preferably 190–2(b) medium, at a density of 25–30 embryoids in each 100×15 mm Petri dish. They are incubated under continuous fluorescent light at room temperature (22° C.). In approximately two weeks, green plantlets develop and are ready for transfer to soil. Green plants are raised in the greenhouse, much like plants grown from seeds. If plants appear to be haploid, colchicine can be applied to induce chromosome doubling. Seeds produced on any plants are instantly homozygous, and so can immediately be used for rapid evaluation and selection in breeding, for analyses in genetics research, or for selection and evaluation of transformants in biotechnology.

EXAMPLE 2

The Effect of 2-HNA Concentration on Induction of the Formation of Embryoids and on Green Plant Regeneration Experiments were conducted to evaluate the effect of 2-HNA on embryoid induction and green plant regeneration. Plant material was treated in accordance with the methods set forth in Example 1, except as described herein. Tillers of wheat cultivar Chris were treated with 2-HNA at concentrations of 0, 1, 10 or 100 mg/l. Three tillers were utilized for each concentration of 2-HNA.

Chris tillers were placed in sterile flasks and incubated with 2-HNA dissolved in sterile water at 33° C. for 66 hours before blending to release the microspores. As an option to ease the work schedule, newly sampled tillers may be incubated with 2-HNA at 4° C. for up to 72 hrs prior to the 33° C. treatment. Isolated microspores were cultured in 60×15 mm Petri dishes each containing 5 ml of medium NPB 98–1, including 1 mg/l phenylacetic acid (PAA) and incubated at 27° C. The regeneration medium was 190–2. Five fresh, live, Chris ovaries per Petri dish were included in each Petri dish.

As set forth in Table 2 below, the number of induced embryoids increases with increasing concentrations of 2-HNA, while the percentage of regenerated green plants (expressed as a percentage of the number of embryoids transferred to regeneration medium) does not significantly differ between different concentrations of 2-HNA.

TABLE 2

Embryoid yields and percentage of green plants from microspores treated with various concentrations of 2-HNA

| Treatment | 2-HNA (mg/l) | 0 | 1 | 10 | 100 |
|---|---|---|---|---|---|
| Number of embryoids | rep 1 | 2 | 219 | 142 | 1258 |
| | rep 2 | — | 16 | 501 | 1217 |
| | mean | 2 | 118 | 322 | 1238 |
| green plant (%) | rep 1 | 0 | 100 | 100 | 100 |
| | rep 2 | — | — | 94 | 100 |
| | mean | 0 | 100 | 97 | 100 |

Note: fresh ovaries were not added to the induction medium after the first transfer of embryoids to regeneration medium, therefore most of the remaining embryoids began to die after the first transfer. The abbreviation "rep" refers to each repeat experiment.

EXAMPLE 3

Optimization of 2-HNA Concentration Utilizing Wheat Cultivar Pavon 76

Experiments were conducted to optimize the amount of 2-HNA utilized to stimulate androgenesis and regeneration of green plants. Plant material was treated in accordance with the methods set forth in Example 1, except as described herein. Tillers of wheat cultivar Pavon 76 were treated with 2-HNA at concentrations of 0, 100, 500 or 1000 mg/l. Two tillers were utilized per treatment.

Tillers were placed in sterile flasks containing 50 ml 2-HNA solution and incubated at 33° C. for 46 hours before blending to release microspores. Microspores were again cultured in 60×15 mm Petri dishes, each containing 5 ml medium NPB 98-1 and incubated at 27° C. The regeneration medium was 190-2. Five fresh, live, immature Pavon 76 ovaries per Petri dish were included in each Petri dish.

As set forth in Table 3, both the number of induced embryoids and the percentage of regenerated green plants (expressed as a percentage of the number of embryoids transferred to regeneration medium) were highest at a 2-HNA concentration of 100 mg/l.

TABLE 3

Embryoid yield and percentage of green plants produced by microspores treated with various concentrations of 2-HNA

| | 2-HNA (mg/l) | 0 | 100 | 500 | 1000 |
|---|---|---|---|---|---|
| # embryoids | rep1 | 153 | 603 | 119 | 320 |
| | rep2 | 15 | 2109 | 13 | 1216 |
| | mean | 84 | 1356 | 66 | 768 |
| green plant (%) | rep1 | — | 67 | 33 | 22 |
| | rep2 | — | 60 | — | 40 |
| | mean | — | 63 | 33 | 31 |

Note: fresh ovaries were not added to the induction medium after the first transfer of embryoids to regeneration medium, therefore most of the remaining embryoids began to die after the first transfer. The abbreviation "rep" refers to each repeat experiment.

EXAMPLE 4

Optimization of 2,4-D Concentration Using Wheat Cultivar Chris

Experiments were conducted to optimize the amount of 2,4-D utilized to enhance androgenesis and regeneration of green plants. Plant material was treated in accordance with the methods set forth in Example 1, except as described herein. Tillers of wheat cultivar Chris were treated with 2,4-D at concentrations of 0.2, 22.1, or 221 mg/l plus a fixed dose of 2-HNA at 100 mg/l. Two tillers were utilized per treatment.

Tillers in flasks with 2-HNA, plus different 2,4-D doses were placed at 33° C. for 70 hours before blending to release microspores. Microspores were cultured in 60×15 mm Petri dishes, each containing 5 ml medium NPB 98-1 plus 1 mg/l 2,4-D and incubated at 27° C. The regeneration medium was 190-2. Five fresh, live, immature Chris ovaries per Petri dish were included in each Petri dish.

As shown in Table 4 below, both the number of induced embryoids and the percentage of regenerated green plants (expressed as a percentage of the number of embryoids transferred to regeneration medium) were highest with a 2,4-D concentration of 1 mg/l during the pretreatment. The abbreviation "rep" in Table 4 refers to each repeat experiment.

TABLE 4

Embryoid yield and percentage of green plants generated by microspores treated with various 2,4-D concentrations

| Pretreatment | 2,4-D (mg/l) | 0.2 | 22.1 | 221 |
|---|---|---|---|---|
| | 2-HNA (mg/l) | 100 | 100 | 100 |
| Induction medium (NPB98-1) | 2,4-D (mg/l) | 1 | 1 | 1 |

TABLE 4-continued

Embryoid yield and percentage of green plants generated
by microspores treated with various 2,4-D concentrations

| Number of embryoids | rep1 | 2107 | 1156 | 0 |
| --- | --- | --- | --- | --- |
| | rep2 | 2088 | 1908 | 0 |
| | mean | 2098 | 1532 | 0 |
| Green plant (%) | rep1 | 83 | 63 | — |
| | rep2 | 100 | 79 | — |
| | mean | 92 | 71 | — |

EXAMPLE 5

Optimization of the Concentration of 2,4-D Using Wheat Cultivar Pavon 76

Experiments were conducted to optimize the amount of 2,4-D utilized to induce androgenesis and regeneration of green plants. Plant material was treated in accordance with the methods set forth in Example 1, except as described herein. Spikes of wheat cultivar Pavon 76 were treated with 2,4-D at concentrations of 0, 0.2, 2.2, or 22.1 mg/l plus a fixed dose of 2-HNA at 100 mg/l. Two spikes were utilized per treatment.

Spikes were incubated in sterile flasks with 2-HNA plus different doses of 2,4-D. The flasks were incubated at 33° C. for 46 hours before blending to release microspores. Microspores were cultured in 6-cm Petri dishes, each containing 5 ml medium NPB 98-1 plus 0 or 0.2 mg/l 2,4-D and incubated at 27° C. The regeneration medium was 190-2. Five fresh, live, immature Chris ovaries per Petri dish were included in each Petri dish.

As shown in Table 5, both the number of induced embryoids and the percentage of regenerated green plants (expressed as a percentage of the number of embryoids transferred to regeneration medium) were highest with a 2,4-D concentration of 2.2 mg/l during the pretreatment. The abbreviation "rep" in Table 5 refers to each repeat experiment.

TABLE 5

Embryoid yield and percentage of green plants generated by Pavon 76
microspores pretreated with various concentrations of 2,4-D

| Pretreatment | 2,4-D (mg/l) | 0 | 0.2 | 2.2 | 22.1 |
| --- | --- | --- | --- | --- | --- |
| | 2-HNA (mg/l) | 100 | 100 | 100 | 100 |
| Induction medium (NPB98-1) | 2,4-D (mg/l) | 0 | 0.2 | 0.2 | 0.2 |
| Number of embryoids | rep1 | 607 | 1121 | 1634 | 1012 |
| | rep2 | 603 | 1200 | 1675 | 1119 |
| | mean | 605 | 1161 | 1655 | 1066 |
| Green plant (%) | rep1 | 13 | 9 | 31 | 0 |
| | rep2 | 25 | 9 | 28 | 35 |
| | mean | 19 | 9 | 30 | 18 |
| Doubled-Haploid % | Rep 1 | 0 | 33 | 50 | — |
| | Rep 2 | 50 | 67 | 38 | 17 |

EXAMPLE 6

Culture Media

The media set forth in Table 6 are useful in the practice of the present invention. In particular, media NPB98-1 and NPB-99 are novel media of the present invention and are preferably used to coculture treated microspores with plant ovaries. Medium 190-2(b) is preferably used to culture embryoids during their development into green plants. Other media, except for MB-97, described in Table 6 are those commonly reported in the literature, but which have been found to be comparatively ineffective for production of embryoids. MB-97 is a novel medium of the present invention and is nearly as effective as NPB98-1 when used to coculture treated microspores with plant ovaries. The values for the amount of each medium component are milligrams per liter.

TABLE 6

| Chemical (mg/L) | NPB98 | MB97 | A2 | LM94+ | MS | CHB-2 | MMS-2 | NPB-A | 190-2 | NPB-99 | 190-2(b) |
| --- | --- | --- | --- | --- | --- | --- | --- | --- | --- | --- | --- |
| $NH_4NO_3$ | | | | 300 | 1650 | | 300 | | | | |
| $(NH_4)_2SO_3$ | 232 | 232 | 231.5 | | | 232 | | | 200 | 232 | 200 |
| $KNO_3$ | 1415 | 1415 | 1415 | 1400 | 1900 | 1415 | 1400 | | 1000 | 1415 | 1000 |
| $CaCl_2-2H_2O$ | 83 | 83 | 83 | 150 | 332.2 | 83 | 440 | 148 | | 83 | |
| $Ca(NO_3)2-4H_2O$ | | | | | | | | | 100 | | 100 |
| $KH_2PO_4$ | 200 | 200 | 200 | 400 | 170 | 200 | 170 | 136 | 300 | 200 | 300 |
| $MgSO_4-7H_2O$ | 93 | 93 | 92.5 | 150 | 180.7 | 93 | 370 | 246 | 200 | 93 | 200 |
| KCl | | | | | | | | 1492 | 40 | | 40 |
| $Na_2EDTA$ | 37.3 | 37.3 | | 37.3 | 37.3 | 37.3 | 37.3 | | 37.3 | 37.3 | 37.3 |
| $FeSO_4-7H_2O$ | 27.8 | 27.8 | | 27.8 | 27.8 | 27.8 | 27.8 | | 27.8 | 27.8 | 27.8 |
| Fe—NaEDTA | | | 32 | | | | | 56 | | | |
| $H_3BO_3$ | 5 | 5 | 1.5 | 6 | 6.2 | 5 | 6.2 | 3 | 3 | 5 | 3 |
| $CoCl-6H_2O$ | 0.0125 | 0.0125 | 0.0125 | 0.025 | 0.025 | 0.0125 | 0.025 | | | 0.0125 | |
| $CuSO_4-5H_2O$ | 0.0125 | 0.0125 | 0.0125 | 0.025 | 0.025 | 0.0125 | 0.025 | | | 0.0125 | |
| KI | 0.4 | 0.4 | 0.375 | 0.8 | 0.83 | 0.4 | 0.83 | 0.5 | 0.5 | 0.4 | 0.5 |
| $MnSO_4-H_2O$ | 5 | 5 | 5 | 11 | 16.9 | 5 | 16.9 | | | | |
| $MnSO_4-4H_2O$ | 5 | 5 | | | | | | 8 | 8 | 5 | 8 |
| $Na_2MoO_4-2H_2O$ | 0.0125 | 0.0125 | 0.0125 | | 0.25 | 0.0125 | 0.25 | | | 0.0125 | |
| $ZnSO_4-7H_2O$ | 5 | 5 | 1 | 9 | 8.6 | 5 | 8.6 | 0.3 | 3 | 5 | 3 |
| Myo inositol | 50 | 50 | 50 | | | 300 | 100 | | 100 | 50 | 100 |
| Glycine | | | | 1 | | 1 | | | 2 | | 2 |
| Nicotinic Acid | 0.5 | 0.5 | 0.5 | 0.5 | | 0.25 | 0.5 | | 0.5 | 0.5 | 0.5 |
| Pyridoxine-HCL | 0.5 | 0.5 | 0.5 | 0.5 | | 0.5 | 0.5 | | 0.5 | 0.5 | 0.5 |
| Thiamine-HCL | 5 | 5 | 5 | 1 | | 2.5 | 0.4 | | | 5 | |
| MES | | | | 200 | | | | | | | |
| Sucrose | | | | | | | | | 30,000 | | 30,000 |

TABLE 6-continued

| Chemical (mg/L) | NPB98 | MB97 | A2 | LM94+ | MS | CHB-2 | MMS-2 | NPB-A | 190-2 | NPB-99 | 190-2(b) |
|---|---|---|---|---|---|---|---|---|---|---|---|
| Maltose | 90,000 | 90,000 | 90,000 | 94,000 | | 90,000 | 90,000 | 90,000 | | 90,000 | |
| Ascorbic Acid | | | | | | 0.5 | | | | | |
| Biotin | | | | 1 | | 0.25 | | | | | |
| Casein Hydrolysate | | | | 100 | | | | | | | |
| Calcium Pantothenate | | | | | | 0.25 | | | | | |
| Glutamine | 500 | 500 | 500 | 500 | | 1 | 146 | | | 500 | |
| Kinetin | | | | | | 0.5 | 0.5 | 0.5 | | 0.2 | |
| 2,4-D | | 1 | | 2 | | 1 | | | | 0.2 | |
| PAA | 1 | | | | | | 4 | | | 1 | |
| NAA | | | | 1 | | | | | | | |
| Gelrite | | | | | | | | | 3,000 | | 3,000 |

EXAMPLE 7

Use of Plant Ovary Conditioned Medium Instead of Live Plant Ovaries in the Practice of the Present Invention In the practice of the present invention stressed microspores are cocultured with either ovary-conditioned medium or at least one live plant ovary (although it is within the scope of the present invention to coculture stressed microspores with both ovary-conditioned medium and at least one live plant ovary).

In order to test if media conditioned with ovaries will support the embryogenic development of microspores to completion, ovaries were excised and placed into Petri dishes supplemented with NPB-98 medium. The density of ovaries in the Petri dishes was initially set at ten ovaries per milliliter of medium. After being sealed with parafilm, all Petri dishes were incubated at 27° C. for a period of 2 through 45 days, during which the conditioned medium was removed from various dishes at various time points. The removed medium was then mixed with NPB-98 (in a 1:3 ratio) and microspores were isolated. The microspore cultures were maintained at 27° C. and examined with an inverted microscope periodically to monitor cell divisions and embryogenic development. Data on the numbers of initial embryogenic microspores, percentage of dividing cells, percentage of proembryoids and of embryoids were collected. The rate of embryoid development was also measured at various time points during culture.

The results of these experiments are shown in Table 7. One dose (1:3 dilution in NPB-98) of ovary conditioned medium was able to support microspore division and carry embryogenesis to completion. Media conditioned with ovaries for 4–21 days were able to sustain microspore embryogenesis. Media conditioned with ovaries for 4 weeks or longer was not able to sustain the cell divisions required to form embryoids, although slow and limited cycles of cell divisions were observed even with 40 d old ovary medium.

TABLE 7

The Effectiveness of Ovary Conditioned Media in Maintaining Embryogenesis of Freshly Isolated Microspores from Wheat Variety Chris

| Conditioning Period (d) | 40 | 37 | 28 | 21 | 14 | 7 | Ovary |
|---|---|---|---|---|---|---|---|
| 2 d Observation* | −MFC | −MFC | −MFC | +MFC | ++MFC | ++MFC | −MFC |
| Embryogenic Total %** | 20 | 19 | 19 | 22 | 29 | 50 | 41 |
| Cell Division % | 10 | 11 | 9 | 18 | 19 | 31 | 41 |
| Proembryoids % | 0.8 | 3.8 | 4.2 | 9.1 | 10.8 | 22.2 | 33.5 |
| Embryoids %[a] | 0 | 0 | 2.2 | 1.9 | 9.5 | 21.9 | 28.7 |

*The observations on the morphology of microspores were made after 48 hrs of induction. "−MFC" means that no microspores with fibrillar cytoplasm were observed, whereas "+MFC" means that some microspores with fibrillar cytoplasm were observed. "++MFC" means a large number of microspores with fibrillar cytoplasm were observed. Fibrillar cytoplasm in microspores is a reliable early indicator for the embryogenic potential of microspores.
**All frequencies were estimated based upon the total population of microspores in culture.
[a]For culture with fresh ovaries, more embryoids were still developing at the time of collecting data, while all embryoids developed from cultures with ovary conditioned medium had reached the size for transfer. These observations indicate that media conditioned with ovaries for an optimum period accelerate the embryogenic development of microspores compared to co-culture with fresh ovaries.

In a separate experiment, ovaries isolated from genotype Pavon 76 were cultured at a density of ten ovaries/ml of NPB-98. After 7, 14, 35 and 40 days in culture, 0.5, 1.0 or 2.0 ml of ovary conditioned medium was added to microspore cultures to a final volume of 3 ml medium. The dilution of aged (35 or 40 d) ovary conditioned media did not show improved microspore embryogenesis, whereas the same dilutions of younger ovary conditioned media led to decreases in frequencies of proembryoids. These results suggest that the functional ingredients released by ovaries are stimulatory rather than inhibitory in nature (Table 8).

TABLE 8

The Effect of Dilution of Ovary Conditioned Media on Microspore Embryogenesis

| | Conditioning Period (d) | | | | | | | | | | | |
|---|---|---|---|---|---|---|---|---|---|---|---|---|
| | 40 | | | 35 | | | 14 | | | 7 | | |
| Conditioned Medium (ml) | 0.5 | 1.0 | 2.0 | 0.5 | 1.0 | 2.0 | 0.5 | 1.0 | 2.0 | 0.5 | 1.0 | 2.0 |
| Embryogenic Cell % | 8 | 10 | 12 | 21 | 20 | 23 | 29 | 21 | 44 | 49 | 46 | 52 |
| Proembryoid % | 0.2 | 0.8 | 0.7 | 2.5 | 3.8 | 3.5 | 13 | 16 | 22 | 17 | 22 | 31 |
| Embryoid %** | | | | | | | | | | | | |

**Data on mature embryoids were not available. However, through repeated early experiments, it is known that the aged media conditioned with ovaries were not able to support microspore embryogenesis to completion while the younger media were able to maintain embryogenesis.

In order to determine the optimum conditioning period of media by ovaries for microspore culture, media conditioned with ovaries at the same density for various time periods were compared with respect to their effectiveness in stimulating microspore embryogenesis. The most effective media were those that were conditioned with ovaries for 7–10 days (d) prior to their use in microspore culture (Table 9). In fact, the ovary conditioned media within this range act to accelerate microspore cell divisions that lead to earlier production of mature embryoids. The first batch of embryoids reached the size of transfer for plant regeneration one week earlier than the control population utilizing fresh ovaries in microspore cultures.

final working concentration in microspore cultures. Microspores were isolated from Pavon 76 as described herein. Five to 30 ovaries per ml of original conditioning medium were all effective, 4 ovaries/ml or below were sub-effective (Table 10). On this basis, the ovary conditioned medium is as effective as the same number of fresh ovaries placed directly in the culture medium at the time cultures are initiated. Twenty ovaries per ml of medium seemed to be most effective, saturating the demand for active ingredients released by cultured ovaries. Ten ovaries per ml worked as well, thirty were no better than twenty. Twenty ovaries per ml of conditioning medium

TABLE 9

The Effect of the Length of Medium Conditioning Period on Embryogenesis of Microspores*

| Conditioning Period (d) | 40 | 37 | 35 | 28 | 21 | 14 | 10 | 7 | 4 | ovary |
|---|---|---|---|---|---|---|---|---|---|---|
| Embryogenic % | 20 | 19 | 17 | 19 | 22 | 34 | 47 | 50 | 49 | 41 |
| Proembryoid % | 0.8 | 3.8 | 2.1 | 4.2 | 9.1 | 16 | 25.8 | 22.2 | 26.2 | 33.5 |
| Embryoid % | 0 | 0 | 0 | 2.2 | 1.9 | 15.5 | 23.4 | 21.9 | 16.3 | 28.7 |

*Microspores were isolated from Pavon 76 while ovaries were obtained from genotype Bob White.

Additionally, a wide range of ovary densities were tested to determine the number of ovaries in the conditioning medium that is most effective for stimulating microspore embryogenesis once the conditioning medium is diluted to a (subsequently diluted three-fold to achieve a working concentration) is effective for all wheat genotypes tested thus far, including Pavon 76, Chris, WED 202; 16-2, Bob White and WPB 926.

TABLE 10

The Effectiveness of Media Conditioned by Ovaries at Various Densities

| Ovaries/ml | Ovary | 2 | 5 | 10 | 15 | 20 | 25 | 30 |
|---|---|---|---|---|---|---|---|---|
| 2 d Observation* | −MFC | −MFC | −MFC | +MFC | +MFC | ++MFC | ++MFC | ++MFC |
| Embryogenic Total % | 41.3 | 3.1 | 31.8 | 50.0 | 41.7 | 49.5 | 51.2 | 47.3 |
| Proembryoid % | 33.5 | <0.5 | 13.7 | 22.2 | 20.8 | 24.9 | 23.8 | 25.4 |
| Embryoid % | 14.7** | 0 | 11.6 | 21.9 | 18.2 | 23.6 | 23.1 | 22.7 |

*Observations were made using an inverted microscope 2 days (d) after the initiation of culture.
"−MFC" represents no microspores with fibrillar cytoplasm; "+MFC" indicates the presence of some microspores with fibrillar cytoplasm; "++MFC" represents the presence of a large number of microspores with fibrillar cytoplasm.
**At the time that these data were collected, petri dishes supplemented with fresh ovaries rather than extract had more embryoids growing but these had not yet reached the size for transfer.

In order to determine the effect of ovary genotype on the effectiveness of ovary-conditioned medium in the practice of the present invention, ovaries were excised from various genotypes and were tested for their effectiveness in stimulating microspore embryogenesis. Microspores were isolated from wheat variety Chris. The available data do not show genotype differences. Media conditioned with ovaries from all genotypes, ranging from early uninucleate through mature pollen were all effective for promoting the production of proembryoids from microspores. The density of ovaries and the time they were cultured in the conditioning medium were more critical than the genotype and the developmental stage of ovaries at the time of excision. Ten ovaries per ml of medium conditioned for a period of 7–14 days, and subsequently diluted three fold for microspore culture were the most beneficial for embryoid development.

EXAMPLE 8

Reducing the Number of Albino Plants

Although the methods of the present invention produce high yields of embryoids from the microspores of a wide range of plant species, embryoids from some plant genotypes yield a high percentage of albino plants. Albino plant percentage can be reduced by lower temperature treatment during the temperature stress period, but the total number of embryoids produced is sharply reduced and the total number of green plants produced is consequently low.

The level of nutrients available to the microspores during the nutrient stress step of the methods of the present invention was assessed for its effect on the number of green plants produced. Three spikes of spring wheat line WED 202-16-2 were treated in a flask containing 50 ml of 100 mg/l 2 HNA, 10 mg/l 2,4-D, 2 mg/l BAP, 3 mg/l GA with or without 10% NPB98 induction medium at 33° C. for 69 hours. Microspores were released as described herein. Microspores were cultured in 5 ml of NPB98 induction media in 6 cm Petri dishes at a density of 30,000 microspores per ml induction medium. Four fresh ovaries of WED 202-16-2 were added to each of the Petri dishes. There were 2 replications for each treatment. The results are shown in Table 11.

TABLE 11

| Pretreatment media in flask | | With 10% NPB98 | Without 10% NPB98 |
|---|---|---|---|
| number of embryoids | Rep1 | 500 | 500 |
| | Rep2 | 500 | 500 |
| | Mean | 500 | 500 |
| number of 1st group of embryoids transferred to 190-2 | Rep1 | 50 | 50 |
| | Rep2 | 50 | 50 |
| | Mean | 50 | 50 |
| number of green plants | Rep1 | 30 | 21 |
| | Rep2 | 40 | 23 |
| | Mean | 35 | 22 |
| Green plant regenerant (%) | Rep1 | 97 | 70 |
| | Rep2 | 95 | 70 |
| | Mean | 96 | 70 |
| number of albino plants | Rep1 | 1 | 9 |
| | 1 Rep2 | 2 | 10 |
| | Mean | 2 | 10 |
| Albino plant regenerant (%) | Rep1 | 3 | 30 |
| | Rep2 | 5 | 30 |
| | Mean | 4 | 30 |
| number of 2nd & 3rd group of embryoids* transferred to 190-2 | Rep1 | 65 | 65 |
| | Rep2 | 65 | 65 |
| | Mean | 65 | 65 |

TABLE 11-continued

| Pretreatment media in flask | | With 10% NPB98 | Without 10% NPB98 |
|---|---|---|---|
| number of green plants | Rep1 | 32 | 23 |
| | Rep2 | 42 | 32 |
| | Mean | 37 | 28 |
| Green plant regenerant (%) | Rep1 | 82 | 70 |
| | Rep2 | 84 | 71 |
| | Mean | 83 | 71 |
| number of albino plants | Rep1 | 5 | 10 |
| | Rep2 | 8 | 13 |
| | Mean | 7 | 12 |
| Albino plant regenerant (%) | Rep1 | 18 | 30 |
| | Rep2 | 16 | 29 |
| | Mean | 17 | 30 |

*When transferring the first group of embryoids, all culture plates were refreshed with 2.5 ml new NPB98 induction media, and the old ovaries were also replaced with fresh ovaries from the genotype Chris at a density of five ovaries per plate.

The results clearly show that the addition of 10% NPB98 induction medium in the pretreatment medium resulted in an increase of total green plant production, and a decrease of albino plant formation.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of producing rice plants from rice microspores comprising:
   (a) selecting rice plant material including rice microspores at a developmental stage amenable to androgenic induction;
   (b) subjecting said microspores to temperature stress to obtain stressed microspores;
   (c) contacting said microspores with an amount of a sporophytic development inducer effective to induce sporophytic development, said contacting step occurring before, during, after, or overlapping with any portion of said temperature stress step;
   (d) isolating said stressed and contacted microspores;
   (e) coculturing said isolated microspores with either ovary-conditioned medium or at least one live plant ovary; and
   (f) producing rice plants from the cocultured microspores.

2. The method of claim 1 wherein the microspores within the selected plant material are in the mid uninucleate to early binucleate stage of development.

3. The method of claim 1 wherein the microspores are subjected to temperature stress by incubating the selected plant material including said microspores at a temperature of from about 4° C. to about 43° C.

4. The method of claim 3 wherein the selected plant material including the microspores is incubated at a temperature of about 33° C.

5. The method of claim 3 wherein the microspores are subjected to temperature stress for a period of from about half an hour to about 72 hours.

6. The method of claim 1 further comprising the step of subjecting the microspores to nutrient stress by contacting the selected plant material including said microspores with an aqueous medium comprising an amount of at least one nutrient that is less than the amount of that nutrient necessary for the optimal growth and development of the microspores in the aqueous medium, said nutrient stress step occurring before, during, after, or overlapping with any portion of said temperature stress step.

7. The method of claim 6 wherein said aqueous medium comprises a dilution of NPB 98 that is less than or equal to 80% of its undiluted concentration.

8. The method of claim 1 wherein said sporophytic development inducer is selected from the group consisting of 2-aminonicotinic acid; 2-chloronicotinic acid; 6-chloronicotinic acid; 2-chloroethyl-phosphonic acid; 2-hydroxynicotinic acid; 6-hydroxynicotinic acid; 3-hydroxypicolinic acid; Benzotriazole; 2-hydroxyproline; 2,2'-dipyridil; 2,4-pyridine dicarboxylic acid monohydrate; 2-hydroxypyridine; 2,3-dihydroxypyridine; 2,4-dihydroxypyrimidine-5-carboxylic acid; 2,4-dihydroxypyrimidine-5-carboxylic acid hydrate; 2-hydroxypirimidine hydrate; 2,4,5-trihydroxypyrimidine; 2,4,6-trichloropyrimidine; 2-hydroxy-4-methyl pyrimidine hydrochloride; 4-hydroxypyrazolo-3,4,d-pyrimidine; quinaldic acid; violuric acid monohydrate; thymine; xanthine; salicylic acid; sodium salicylate; salicyl aldehyde; salicyl hydrazide; 3-chlorosalicylic acid; fusaric acid; picolinic acid; butanediene monoxime; di-2-pyridyl ketone; salicin; 2,2'-dipyridil amine; 2,3,5-triiodobenzoic; 2-hydroxy pyridine-N-oxide; 2-hydroxy-3-nitropyridine; benzotriazole carboxylic acid; salicyl aldoxime; glycine; D L-histidine; penicillamine; 4-chlorosalicylic acid; 6-aminonicotinic acid; 2,3,5,6-tetrachloride 4-pyridine carboxylic acid; alpha benzoin oxime; 2,3-butadiene dioxime; isonicotinic hydrazide; cupferron; ethyl xanthic acid; 3-hydroxy benzyl alcohol; salicyl amide; salicyl anhydride; salicyl hydroxamic acid; methyl picolinic acid; 2-chloro pyridine; 2,6-pyridine carboxylic acid; 2,3-pyridine dicarboxylic avid; 2,5-pyridine dicarboxylic acid; pichloram; ammonium thiocyanate; amiben; diethyl dithiocarbamate; glyphosate; anthranilic acid; thiourea; 2,4-diclorophenoxyacetic acid; 4-chloro anisole; 2,3-dichloroanisole; 2-(2,4)-dichlorophenoxy propionic acid; 2-(4-chlorophenoxy)-2-methyl propionic acid; 2-(para-chloro phenoxy) isobutyric acid and $\alpha,\beta$-dichlorobutyric acid.

9. The method of claim 8 wherein said sporophytic development inducer is selected from the group consisting of 2-hydroxynicotinic acid, 2-chloroethyl-phosphonic acid, 2-chloronicotinic acid and 2-hydroxyproline.

10. The method of claim 9 wherein said sporophytic development inducer is 2-hydroxynicotinic acid.

11. The method of claim 9 wherein said sporophytic development inducer is 2-chloroethyl-phosphonic acid.

12. The method of claim 1 wherein said sporophytic development inducer is present at a concentration of from about 0.001 mg/l to about 1000 mg/l.

13. The method of claim 1 wherein said sporophytic development inducer is present at a concentration of from about 1 mg/l to about 500 mg/l.

14. The method of claim 1 further comprising the step of contacting said microspores with an effective amount of an auxin, said step of contacting the microspores with an effective amount of an auxin occurring before, during, after, or overlapping with any portion of said temperature stress step.

15. The method of claim 14 wherein said auxin is 2,4-dichlorophenoxyacetic acid.

16. The method of claim 14 wherein said auxin is utilized at a concentration of from about 0.1 mg/l to about 25 mg/l.

17. The method of claim 16 wherein said auxin is utilized at a concentration of from about 0.5 mg/l to about 4.0 mg/l.

18. The method of claim 1 further comprising the step of contacting said microspores with an effective amount of a cytokinin, said step of contacting the microspores with an effective amount of a cytokinin occurring before, during, after, or overlapping with any portion of said temperature stress step.

19. The method of claim 18 in said cytokinin is kinetin.

20. The method of claim 18 wherein said cytokinin consists essentially of benzylaminopurine.

21. The method of claim 18 wherein said cytokinin is utilized at a concentration of from about 0.1 mg/l to about 10 mg/l.

22. The method of claim 21 wherein said cytokinin is utilized at a concentration of from about 0.5 mg/l to about 2.0 mg/l.

23. The method of claim 1 further comprising the step of contacting said microspores with an effective amount of a gibberellin, said step of contacting the microspores with an effective amount of a gibberellin occurring before, during, after, or overlapping with any portion of said temperature stress step.

24. The method of claim 23 wherein said gibberellin is utilized at a concentration of from about 0.01 mg/l to about 20 mg/l.

25. The method of claim 24 wherein said gibberellin is utilized at a concentration of from about 0.2 mg/l to about 4.0 mg/l.

26. The method of claim 1 further comprising the step of contacting said microspores with an effective amount of a cell spindle inhibiting agent, said step of contacting the microspores with an effective amount of a cell spindle inhibiting agent occurring before, during, after, or overlapping with any portion of said temperature stress step.

27. The method of claim 26 wherein said cell spindle inhibiting agent is utilized at a concentration of from about 1 $\mu$M to about 200 $\mu$M.

28. The method of claim 26 wherein said cell spindle inhibiting agent is pronamide.

29. The method of claim 1 wherein said stressed microspores are isolated by density centrifugation.

30. The method of claim 29 wherein said density centrifugation utilizes a solution of mannitol layered over a higher density solution of maltose.

31. The method of claim 1 wherein said coculturing step utilizes a liquid nutrient suspension medium selected from the group consisting of medium NPB98 and NPB-99.

32. The method of claim 1 wherein said coculturing step utilizes at least one live ovary obtained from a plant variety selected from the group consisting of any wheat variety and barley variety Igri.

33. The method of claim 1 wherein said coculturing step utilizes ovary conditioned medium.

34. The method of claim 1 further comprising the step of genetically transforming said microspores.

35. A method of producing rice plants from rice microspores comprising:
  (a) selecting rice plant material including rice microspores at a developmental stage amenable to androgenic induction;
  (b) subjecting said microspores to temperature stress and nutrient stress to obtain stressed microspores;
  (c) contacting said microspores with an effective amount of an auxin, an effective amount of a cell spindle inhibiting agent and an effective amount of a sporophytic development inducer, said contacting step occurring before, during, after, or overlapping with any portion of said temperature and nutrient stress step;
  (d) isolating said stressed and contacted microspores;
  (e) coculturing said isolated microspores with either plant ovary conditioned medium or at least one live plant ovary; and
  (f) producing rice plants from the cocultured microspores.

* * * * *